US012700091B2

(12) United States Patent
Shiroishi

(10) Patent No.: US 12,700,091 B2
(45) Date of Patent: Aug. 4, 2026

(54) MEDICAL IMAGE PROCESSING DEVICE, MEDICAL IMAGE PROCESSING METHOD, AND STORAGE MEDIUM

(71) Applicant: Canon Kabushiki Kaisha, Tokyo (JP)

(72) Inventor: Ryo Shiroishi, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 18/485,789

(22) Filed: Oct. 12, 2023

(65) Prior Publication Data

US 2024/0127441 A1 Apr. 18, 2024

(30) Foreign Application Priority Data

Oct. 14, 2022 (JP) ................................. 2022-165222

(51) Int. Cl.
| | |
|---|---|
| *G06K 9/00* | (2022.01) |
| *A61B 5/00* | (2006.01) |
| *G06T 7/00* | (2017.01) |
| *G16H 30/40* | (2018.01) |

(52) U.S. Cl.
CPC .......... *G06T 7/0012* (2013.01); *A61B 5/4887* (2013.01); *A61B 5/7485* (2013.01); *G16H 30/40* (2018.01); *G06T 2207/30101* (2013.01)

(58) Field of Classification Search
None
See application file for complete search history.

(56) References Cited

U.S. PATENT DOCUMENTS

| | | | |
|---|---|---|---|
| 2012/0209103 A1* | 8/2012 | Sakuragi | G06T 7/0012 600/407 |
| 2018/0243034 A1 | 8/2018 | Yamada | |
| 2023/0086196 A1* | 3/2023 | Denzinger | G16H 50/20 382/131 |

FOREIGN PATENT DOCUMENTS

| | | | |
|---|---|---|---|
| JP | 2018-454 A | 1/2018 | |
| JP | 2018-138124 A | 9/2018 | |
| JP | 2019171151 A * | 10/2019 | G16H 50/50 |
| WO | WO 2017/043150 A1 | 3/2017 | |

OTHER PUBLICATIONS

Matsubara et al., "Automatic whole brain vascular territory mapping", 2020 IEEE, 2020 42nd Annual International Conference of the IEEE Engineering in Medicine & Biology Society (EMBC), doi: 10.1109/EMBC44109.2020.9175261, 4 pages.

* cited by examiner

*Primary Examiner* — Wei Wen Yang
(74) *Attorney, Agent, or Firm* — Oblon, McClelland, Maier & Neustadt, L.L.P.

(57) ABSTRACT

According to an embodiment, a medical image processing device includes processing circuitry. The processing circuitry acquires a medical image obtained by imaging at least an artery. The processing circuitry detects a branch point of the artery on the basis of the medical image. The processing circuitry identifies a dominated region affected by the artery on a downstream side of the branch point in the medical image. The processing circuitry causes a display to display the dominated region.

10 Claims, 12 Drawing Sheets

FIG. 2

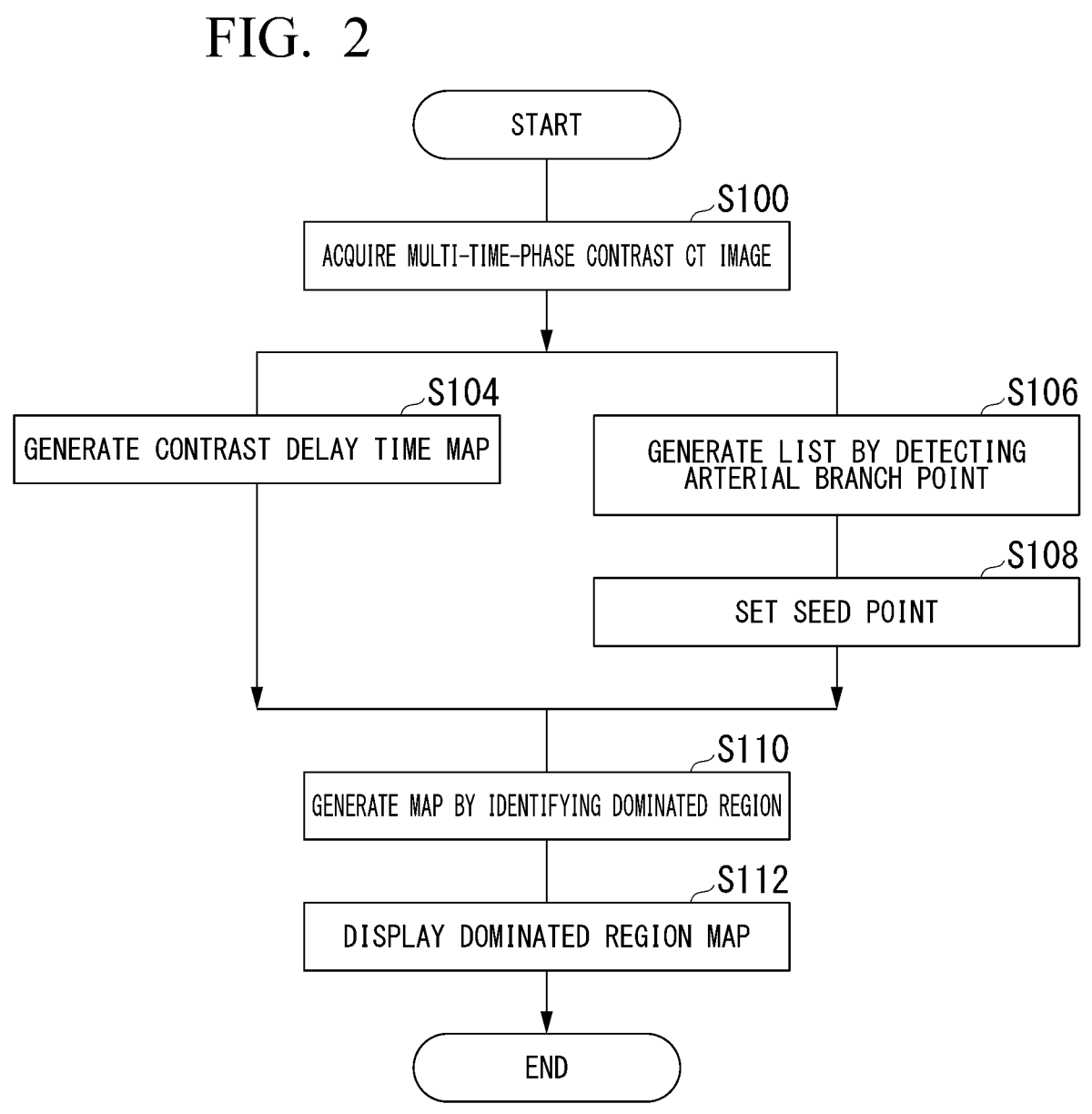

START

S100

ACQUIRE MULTI-TIME-PHASE CONTRAST CT IMAGE

S104

GENERATE CONTRAST DELAY TIME MAP

S106

GENERATE LIST BY DETECTING ARTERIAL BRANCH POINT

S108

SET SEED POINT

S110

GENERATE MAP BY IDENTIFYING DOMINATED REGION

S112

DISPLAY DOMINATED REGION MAP

END

MULTI-TIME-PHASE
CONTRAST CT IMAGE

TIME DENSITY CURVE FOR EACH PIXEL

CONTRAST DELAY TIME MAP

MP2

DOMINATED REGION MAP
(USING ALL SEED POINTS)

MP2

DOMINATED REGION MAP
(USING SOME SEED POINTS)

FIG. 9

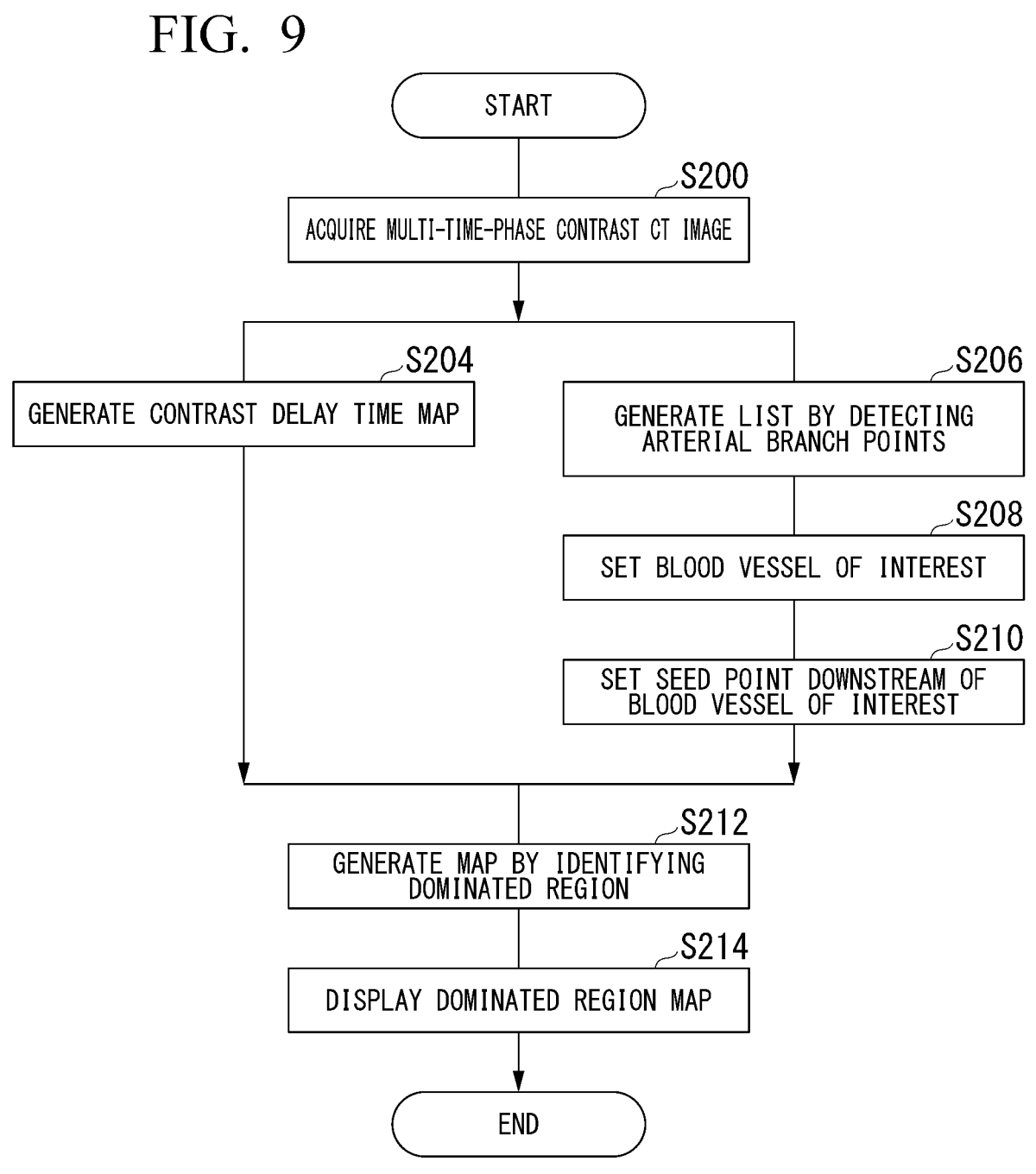

START

S200
ACQUIRE MULTI-TIME-PHASE CONTRAST CT IMAGE

S204
GENERATE CONTRAST DELAY TIME MAP

S206
GENERATE LIST BY DETECTING
ARTERIAL BRANCH POINTS

S208
SET BLOOD VESSEL OF INTEREST

S210
SET SEED POINT DOWNSTREAM OF
BLOOD VESSEL OF INTEREST

S212
GENERATE MAP BY IDENTIFYING
DOMINATED REGION

S214
DISPLAY DOMINATED REGION MAP

END

FIG. 10

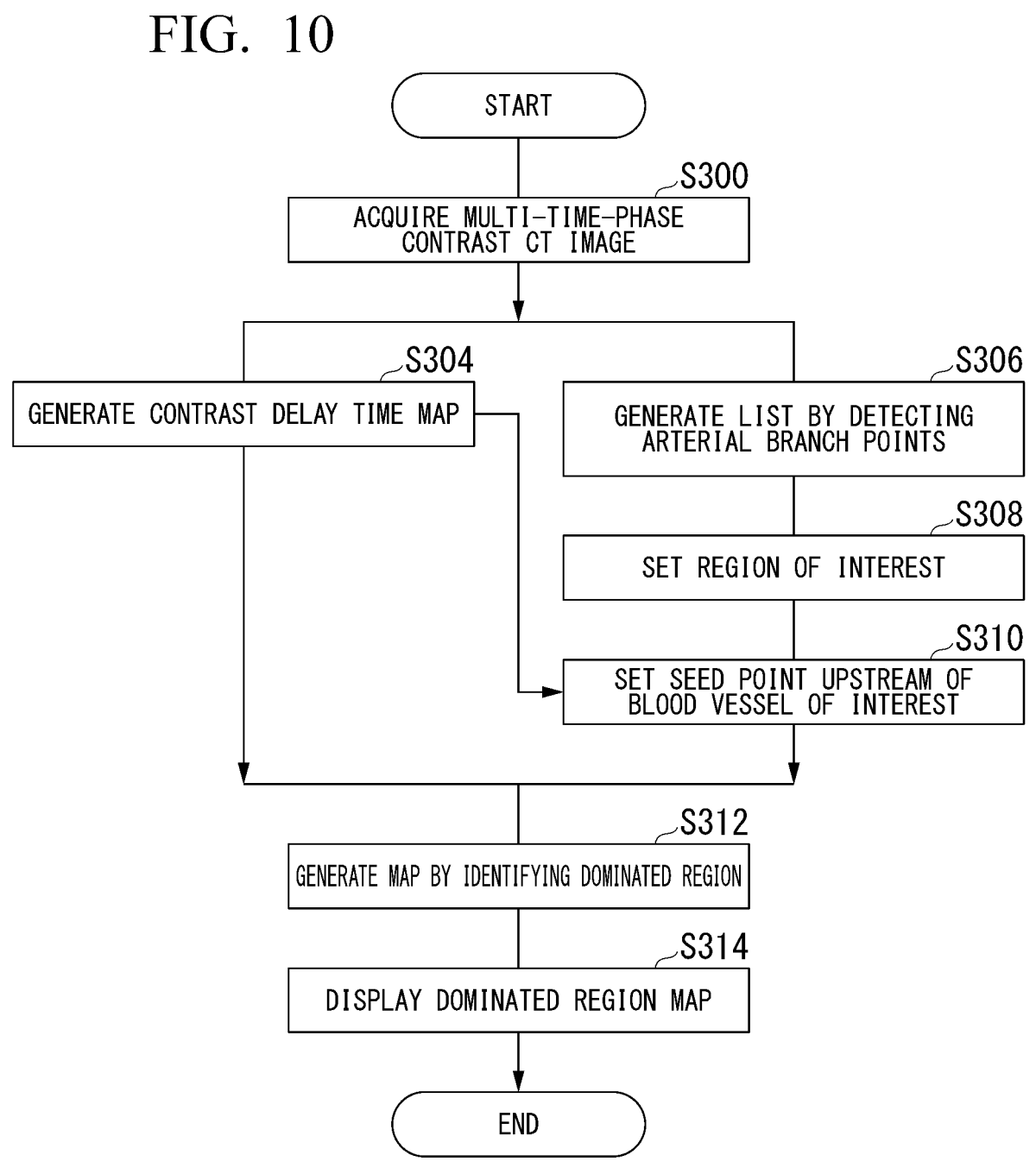

```
                        ┌─────────────┐
                        │    START    │
                        └──────┬──────┘
                               │
                               ▼                    ⌐S300
              ┌────────────────────────────────────┐
              │      ACQUIRE MULTI-TIME-PHASE       │
              │        CONTRAST CT IMAGE            │
              └────────────────┬───────────────────┘
                               │
      ┌────────────────────────┴───────────────────────────┐
      │        ⌐S304                              ⌐S306     │
┌─────────────────────────────────┐   ┌──────────────────────────────┐
│ GENERATE CONTRAST DELAY TIME MAP │──│   GENERATE LIST BY DETECTING  │
└─────────────────────────────────┘   │    ARTERIAL BRANCH POINTS     │
                             │         └───────────────┬──────────────┘
                             │                    ⌐S308
                             │         ┌──────────────────────────────┐
                             │         │      SET REGION OF INTEREST   │
                             │         └───────────────┬──────────────┘
                             │                    ⌐S310
                             │         ┌──────────────────────────────┐
                             └────────▶│ SET SEED POINT UPSTREAM OF    │
                                       │  BLOOD VESSEL OF INTEREST     │
                                       └───────────────┬──────────────┘
                               ┌───────────────────────┘
                               ▼                    ⌐S312
              ┌────────────────────────────────────────────┐
              │ GENERATE MAP BY IDENTIFYING DOMINATED REGION │
              └────────────────┬───────────────────────────┘
                               │                    ⌐S314
              ┌────────────────────────────────────┐
              │     DISPLAY DOMINATED REGION MAP    │
              └────────────────┬───────────────────┘
                               │
                               ▼
                        ┌─────────────┐
                        │     END     │
                        └─────────────┘
```

FIG. 11

MEDICAL IMAGE PROCESSING DEVICE, MEDICAL IMAGE PROCESSING METHOD, AND STORAGE MEDIUM

CROSS-REFERENCE TO RELATED APPLICATION

Priority is claimed on Japanese Patent Application No. 2022-165222, filed Oct. 14, 2022, the content of which is incorporated herein by reference.

FIELD

Embodiments disclosed herein and drawings relate to a medical image processing device, a medical image processing method, and a storage medium.

BACKGROUND

A region where a blood flow of an arterial blood vessel perfuses and nourishes is referred to as a blood vessel-dominated region of each arterial blood vessel. A map in which each blood vessel-dominated region is drawn by color-coding, as if representing the basins of each river by color-coding at the watersheds in a river map, is referred to as a blood vessel-dominated region map.

The blood vessels of the brain mainly include six cerebral arteries (the left and right anterior cerebral arteries, the middle cerebral artery, and the posterior cerebral artery). Vascular territory mapping (VTM) is image processing technology for estimating a blood vessel-dominated region map of the six cerebral arteries using a multi-time-phase contrast CT image as an input. Specifically, a pixel located at the origin of each cerebral artery is used as a seed point and a region expansion method is applied to the contrast delay time image to generate a blood vessel-dominated region map color-coded in six regions.

By using VTM, it is possible to confirm the reduction of the blood vessel-dominated region due to vascular occlusion in a cerebral infarction and the expansion of the blood vessel-dominated region of the cerebral artery that is not occluded. This can be used to determine the severity of a cerebral infarction and the adaptability of treatment.

However, in the conventional technology, it is difficult to identify a dominated region of the blood vessel branching from the cerebral artery. As a result, users have not been able to confirm the dominated region of the branched blood vessel. These problems are not limited to the brain, but are common to all parts where arteries are distributed (for example, the heart, lungs, liver, kidneys, small intestine, and the like).

BRIEF DESCRIPTION OF THE DRAWINGS

FIG. 2 is a flowchart showing a flow of a series of processing steps of processing circuitry according to the first embodiment.

FIG. 9 is a flowchart showing a flow of a series of processing steps of the processing circuitry according to a second embodiment.

FIG. 10 is a flowchart showing a flow of a series of processing steps of the processing circuitry according to a third embodiment.

FIG. 11 schematically shows a series of flows until a blood vessel-dominated region map is generated from a multi-time-phase contrast CT image.

DETAILED DESCRIPTION

Hereinafter, a medical image processing device, a medical image processing method, and a storage medium of embodiments will be described with reference to the drawings. According to an embodiment, a medical image processing device includes processing circuitry. The processing circuitry acquires a medical image obtained by imaging at least an artery. The processing circuitry detects a branch point of the artery on the basis of the medical image. The processing circuitry identifies a dominated region affected by the artery on a downstream side of the branch point in the medical image. The processing circuitry causes a display to display the dominated region. Thereby, it is possible to visualize a dominated region of a blood vessel branching from an artery.

First Embodiment

Figure 1:
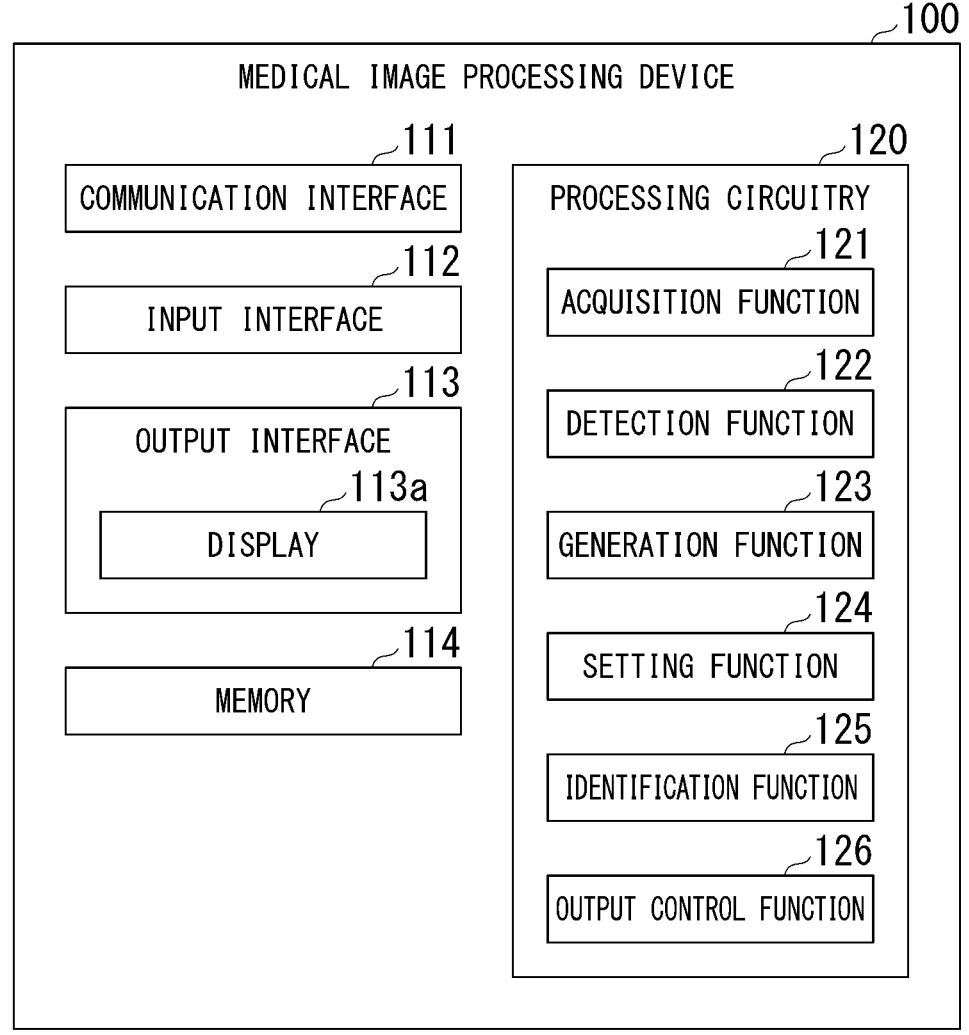
FIG. 1 is a diagram showing an example of a configuration of a medical image processing device in a first embodiment.

[Configuration of medical image processing device] FIG. 1 is a diagram showing an example of a configuration of a medical image processing device 100 in a first embodiment. The medical image processing device 100 includes, for example, a communication interface 111, an input interface 112, an output interface 113, a memory 114, and processing circuitry 120.

The medical image processing device 100 may be a single device or a system in which a plurality of devices connected via a communication network NW operate in cooperation with each other. That is, the medical image processing device 100 may be implemented by a plurality of computers (processors) included in a distributed computing system or a cloud computing system.

The communication interface 111 communicates with a medical image diagnostic device or the like via the communication network NW. The communication interface 111 includes, for example, a network interface card (NIC), an antenna for wireless communication, and the like.

The communication network NW may be a general information and communication network using telecommunication technology. For example, the communication network NW includes a telephone communication circuit network, an optical fiber communication network, a cable communication network, a satellite communication network, and the like as well as a wireless/wired local area network (LAN) such as a hospital-backbone LAN or an Internet network.

The medical image diagnostic device is a modality such as an X-ray computed tomography (CT) device or a magnetic resonance imaging (MRI) device.

The input interface 112 receives various types of input operations from an operator, converts the received input operations into electrical signals, and outputs the electrical signals to the processing circuitry 120. For example, the input interface 112 includes a mouse, a keyboard, a trackball, a switch, a button, a joystick, a touch panel, and the like. The input interface 112 may be, for example, a user interface that receives a sound input such as a microphone. When the input interface 112 is a touch panel, the input interface 112 may have a display function of a display 113a included in the output interface 113 to be described below.

Also, in the present specification, the input interface 112 is not limited to one including physical operation components such as a mouse or a keyboard. For example, electrical signal processing circuitry configured to receive an electrical signal corresponding to an input operation from external input equipment provided separately from the device and output this electrical signal to the control circuit is also included as an example of the input interface 112.

The output interface 113 includes, for example, the display 113a, a speaker 113b, and the like.

The display 113a displays various types of information. For example, the display 113a displays an image generated by the processing circuitry 120, a graphical user interface (GUI) for receiving various types of input operations from the operator, and the like. For example, the display 113a is a liquid crystal display (LCD), a cathode ray tube (CRT) display, an organic electro luminescence (EL) display, or the like.

The speaker 113b outputs information input from the processing circuitry 120 as a sound.

The memory 114 is implemented by a semiconductor memory element such as a random-access memory (RAM) or a flash memory, a hard disk, or an optical disc.

These non-transitory storage media may be implemented by other storage devices connected via the communication network NW such as a network attached storage (NAS) or an external storage server device. Also, the memory 114 may include a non-transitory storage medium such as a read-only memory (ROM) or a register.

The processing circuitry 120 includes, for example, an acquisition function 121, a detection function 122, a generation function 123, a setting function 124, an identification function 125, and an output control function 126. The acquisition function 121 is an example of an "acquisition unit," the detection function 122 is an example of a "detection unit," the generation function 123 is an example of a "generation unit," the setting function 124 is an example of a "setting unit," the identification function 125 is an example of an identification unit," and the output control function 126 is an example of a "display control unit."

In the processing circuitry 120, for example, a hardware processor (a computer) executes a program stored in the memory 114 (storage circuitry) to implement these functions.

The hardware processor in the processing circuitry 120 is, for example, circuitry such as a central processing unit (CPU), a graphics processing unit (GPU), an application-specific integrated circuit (ASIC), or a programmable logic device (for example, a simple programmable logic device (SPLD), a composite programmable logic device (CPLD), or a field programmable gate array (FPGA)). Instead of storing the program in the memory 114, the program may be directly incorporated in the circuitry of the hardware processor. In this case, the hardware processor reads and executes a program incorporated in the circuitry to implement the function. The program may be previously stored in the memory 114 or stored in a non-transitory storage medium such as a DVD or a CD-ROM, and installed in the memory 114 from the non-transitory storage medium when the non-transitory storage medium is loaded in a drive device (not shown) of the medical image processing device 100. The hardware processor is not limited to the configuration of single circuitry and may be configured as a single hardware processor by combining a plurality of pieces of independent circuitry to implement each function. Also, a plurality of components may be integrated into one hardware processor to implement each function.

[Processing Flow of Medical Image Processing Device]

Hereinafter, a series of processing steps of the processing circuitry 120 of the medical image processing device 100 will be described with reference to the flowchart. FIG. 2 is a flowchart showing a flow of the series of processing steps of the processing circuitry 120 according to the first embodiment. In the present flowchart, as an example, it is assumed that a medical image diagnostic device is an X-ray CT device and a medical image is a CT image.

First, the acquisition function 121 is performed to acquire a multi-time-phase contrast CT image IMG1 from the X-ray CT device via the communication interface 111 (step S100). The multi-time-phase contrast CT image IMG1 is a set of CT images obtained when the X-ray CT device continuously images a portion of a patient into whom the contrast medium has been injected a plurality of times. In other words, the multi-time-phase contrast CT image IMG1 is a set of CT images obtained when the X-ray CT device images the portion of the patient into whom the contrast medium has been injected at a plurality of different times. Hereinafter, the portion of the patient imaged by the X-ray CT device will be described as the "brain."

When the multi-time-phase contrast CT image IMG1 is acquired, the generation function 123 is performed to generate a contrast delay time map MP1 on the basis of the multi-time-phase contrast CT image IMG1 (step S104). The contrast delay time map MP1 is an image for visualizing how long it took for the contrast medium to reach each region of the brain.

Figure 3:
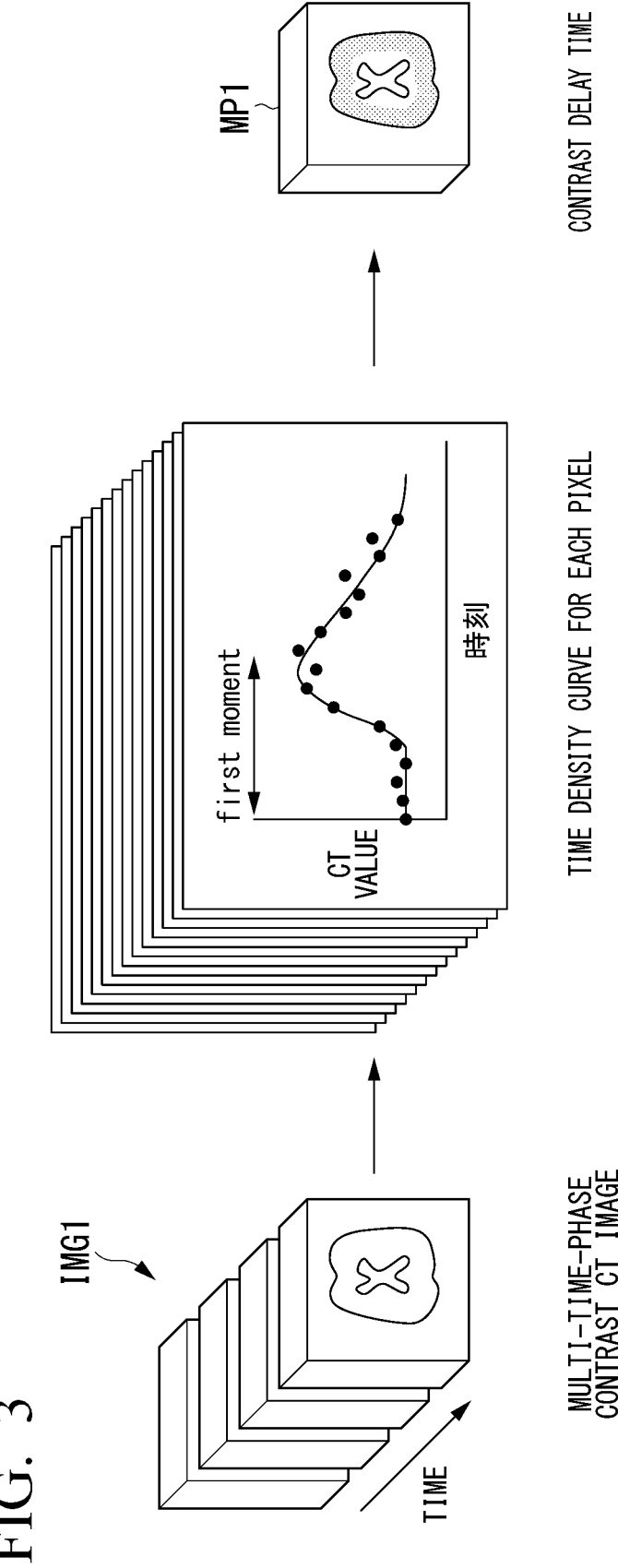
FIG. 3 schematically shows a series of flows until a contrast delay time map is generated from a multi-time-phase contrast CT image.

FIG. 3 is a diagram schematically showing a series of flows until the contrast delay time map MP1 is generated from the multi-time-phase contrast CT image IMG1. First, the generation function 123 is performed to derive a time density curve at each position in the brain from a change over time in the CT value (luminance value) of each pixel of the multi-time-phase contrast CT image IMG1. As shown in FIG. 3, the time density curve is a curve showing how the CT value has changed at each time. For example, the generation function 123 may be performed to derive a time density curve by applying gamma variate function curve fitting with respect to a change in the CT value of each pixel.

Subsequently, the generation function 123 is performed to generate an image in which a first moment of the time density curve (a parameter reflecting a time difference from an adjacent pixel) is a pixel value of each pixel as a contrast delay time map MP1.

Also, the generation function 123 may be performed to generate the contrast delay time map MP1 using another method instead of generating the contrast delay time map MP1 on the basis of the first moment of the time density curve. For example, the generation function 123 may be performed to generate an image in which the time until the rise of the time density curve or the time to peak (the time to the maximum value of the time density curve) is the pixel value of each pixel as the contrast delay time map MP1. Also, for example, the generation function 123 may be performed to obtain a transfer function of the tissue from the time density curve and the arterial input function using a deconvolution method and generate an image in which the time until the rise of the transfer function or Tmax (the time to the maximum value of the transfer function) is a pixel value of each pixel as the contrast delay time map MP1.

On the other hand, when the multi-time-phase contrast CT image IMG1 is acquired, the detection function 122 is performed to detect the branch point B of the artery of the brain on the basis of the multi-time-phase contrast CT image IMG1 and generate the arterial branch point list LT on the basis of the branch point B (step S106). The arterial branch point list LT is a list that represents the connections between the detected branch points B in a data structure.

Figure 4:
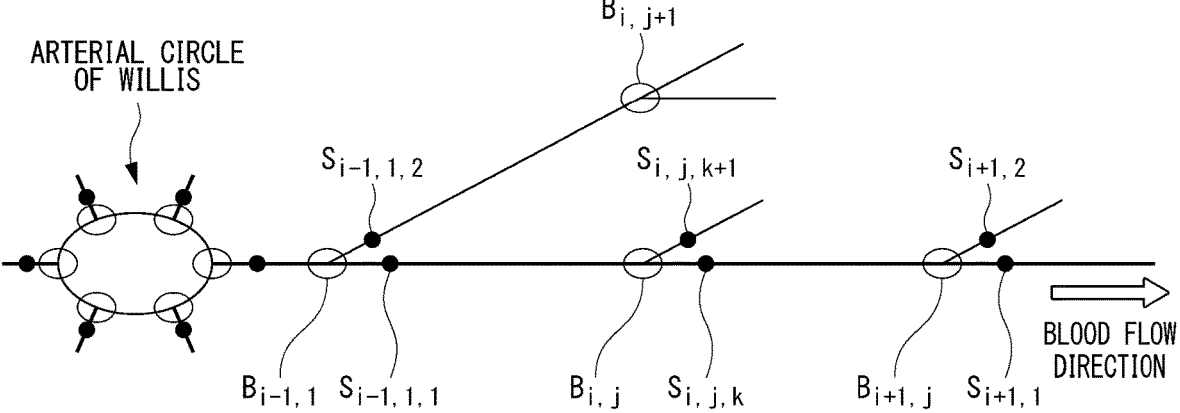
FIG. 4 is a diagram showing an example of an abstracted artery.
Figure 5:
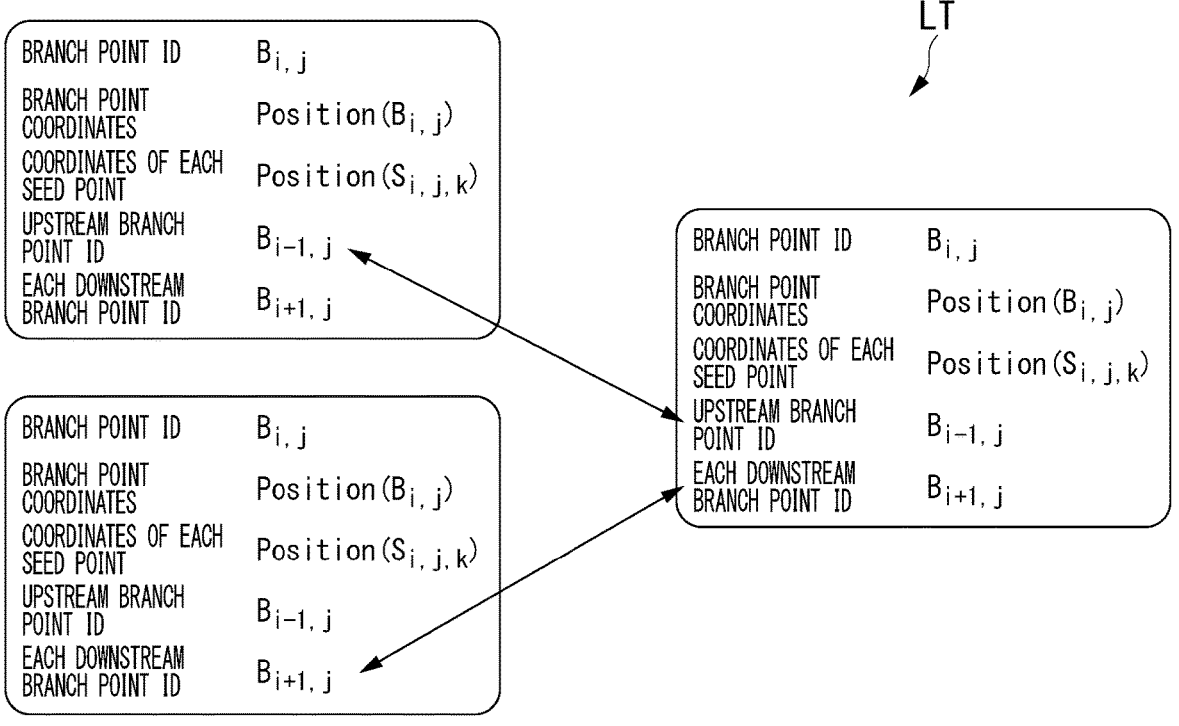
FIG. 5 is a diagram showing an example of an arterial branch point list.
Figure 6:
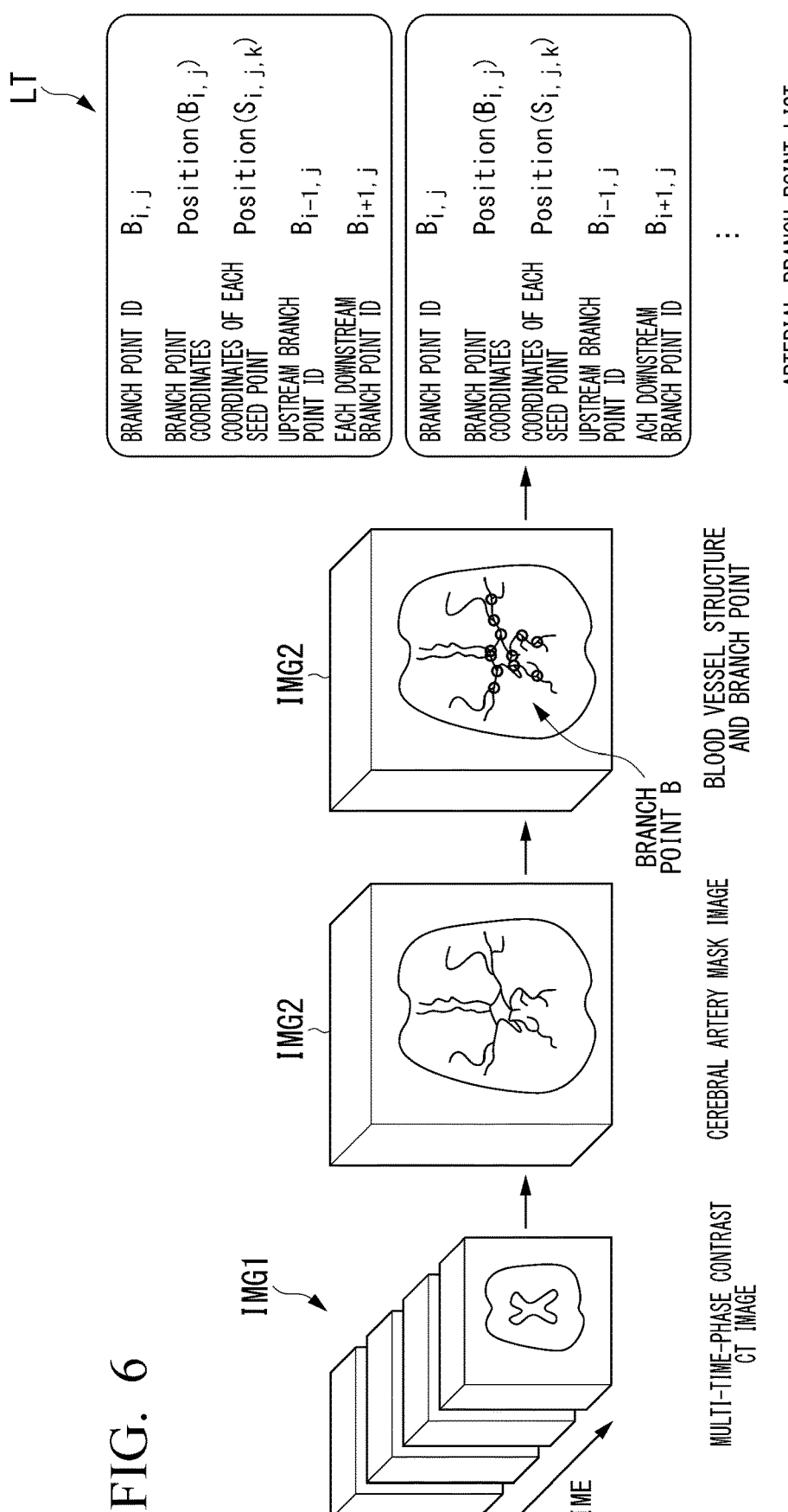
FIG. 6 schematically shows a series of flows until an arterial branch point list is generated from a multi-time-phase contrast CT image.

FIG. 4 is a diagram showing an example of an abstracted artery, FIG. 5 is a diagram showing an example of the arterial branch point list LT, and FIG. 6 is a diagram schematically showing a series of flows until the arterial branch point list LT is generated from the multi-time-phase contrast CT image IMG1.

It is known that the cerebral arteries have a structure that branches from six cerebral arteries toward the periphery (downstream) like the arterial circle of Willis. Therefore, the blood vessels branching from the cerebral artery toward the periphery are considered abstractly as shown in FIG. 4. Specifically, a branch point B where the artery branches and a seed point S for identifying a plurality of branched blood vessels at the branch point B may be set, branch points B or seed points S may be designated as nodes, and the cerebral artery may be abstracted by a graph obtained by connecting the nodes with links.

As shown in FIG. 5, the arterial branch point list LT has information about a branch point ID, branch point coordinates, seed point coordinates, an upstream branch point ID, and a downstream branch point ID for each branch point and has information about connections with upstream and downstream branch points. For example, when attention is paid to branch points $B_{i,j}$, branch points $B_{i-1,1}$ are located on the upstream side of the branch points $B_{i,j}$, and branch points are located on the downstream side thereof. Thus, a branch point with an ID of "$B_{i,j}$" has "$B_{i-1,1}$" in the upstream branch point ID and "$B_{i+1,j}$" in the downstream branch point ID.

As shown in FIG. 6, the detection function 122 is performed to generate a cerebral artery mask image IMG2, which is an image in which only the cerebral artery is extracted, on the basis of the multi-time-phase contrast CT image IMG1. The cerebral artery mask image IMG2 may be generated, for example, by replacing a pixel having a CT value greater than or equal to a threshold value with 1 on a time-phase contrast CT image of a specific range and replacing a pixel having a CT value less than the threshold value with 0 using a contrast timing difference between the artery and others. Also, the cerebral artery mask image IMG2 may be generated by classifying the time density curve of each pixel of the CT image using a time density curve difference between the artery and others, setting a pixel value close to that of the time density curve of the artery to 1, and setting other pixel values to 0.

The detection function 122 is performed to detect the branch point B of the artery by analyzing the structure of the blood vessel on the cerebral artery mask image IMG2. The artery shown in the cerebral artery mask image IMG2 has a tubular structure having a thickness in a three-dimensional image and can be made into a linear structure without thickness in, for example, a three-dimensional thinning process. The detection function 122 is performed to detect the seed point S of each of the six cerebral artery origins on the basis of an anatomical structure of the blood vessel from the multi-time-phase contrast CT image IMG1 using the method of Non-Patent Document 1.

The detection function 122 is performed to scan the pixel values of the cube region of 3×3×3 along the line from the seed point S of each cerebral artery origin, and detects a point where four or more pixels of the cube region have a value as the branch point B. That is, the detection function 122 is performed to search for a branch point B from the upstream of the artery.

Also, the detection function 122 may be performed to scan the pixel values of the cubic region of 3×3×3 from the end of the artery and designate a seed point of each branch point B having a connection (corresponding to the arterial circle of Willis) to circulate finally as a seed point S of each cerebral artery origin. That is, the detection function 122 may be performed to search for the branch point B from the downstream of the artery instead of searching for the branch point B from the upstream of the artery.

The detection function 122 is performed to assign a number to each branch point B, set the number as a branch point ID, set a position in the image space as coordinates of the branch point B, and set a point slightly moved from the branch point B along the line (along the blood vessel) in the terminal direction (downstream direction) as coordinates of each seed point S. Also, the detection function 122 is performed to set numbers of adjacent branch points B on the upstream side and the downstream side as an upstream branch point ID and a downstream branch point ID with respect to each branch point B. The detection function 122 is performed to store these in a connection list and generate an arterial branch point list LT.

The description returns to the flowchart of FIG. 2. Subsequently, the setting function 124 is performed to set some or all of the plurality of seed points S in which coordinate points are stored in the arterial branch point list LT as a seed point serving as the starting point of the region expansion method on the contrast delay time map MP1 (hereinafter referred to as an expanded seed point S #) (step S108).

For example, the setting function 124 may be performed to set all of the plurality of seed points S as expanded seed points S #. Thereby, a dominated region of all branched blood vessels can be visualized. Also, the setting function 124 may be performed to set some of the plurality of seed points S as the expanded seed point S #. Thereby, only the dominated region of some branched blood vessels can be visualized.

Subsequently, the identification function 125 is performed to identify the dominated region of each branched blood vessel on the basis of the expanded seed point S #set on the contrast delay time map MP1 and generate a blood vessel-dominated region map MP2 by visualizing the dominated region of each branched blood vessel (step S110). The dominated region as described above is a region where the blood flow of the blood vessel is perfused and nourished.

For example, the identification function 125 may be performed to generate the blood vessel-dominated region map MP2 by color-coding each region of the contrast delay time map MP1 with a different pixel value for each expanded seed point S #set on the contrast delay time map MP1 using the region expansion method.

The region expansion method is a general image region division method in which nearby pixels of a region to which the expanded seed point S #belongs are scanned and a region with similar pixel values is color-coded as a region identical to that of the expanded seed point S #. The contrast delay time map MP1 has a delay period of time from the start of contrast to the occurrence of the contrast effect as a pixel value. A region located downstream of an expanded seed point S #has a longer delay period of time than its upstream region. Therefore, the identification function 125 is performed to perform a region expansion process in a region where pixel values are close to each other and large. For the seed point S of the adjacent upstream branch point B and the adjacent downstream branch point B, an upstream-dominated region includes a downstream-dominated region in principle. Therefore, it is assumed that the identification function 125 does not allow the upstream region to which the expanded seed point S #belongs to extend to the downstream region to which the expanded seed point S #belongs.

Subsequently, the output control function 126 causes the display 113a of the output interface 113 to display the blood vessel-dominated region map MP2 (step S112). Also, the output control function 126 may be performed to transmit the blood vessel-dominated region map MP2 to an external display device via the communication interface 111 in addition to or in place of displaying the blood vessel-dominated region map MP2 on the display 113a. With this, the process of the present flowchart ends.

Figure 7:
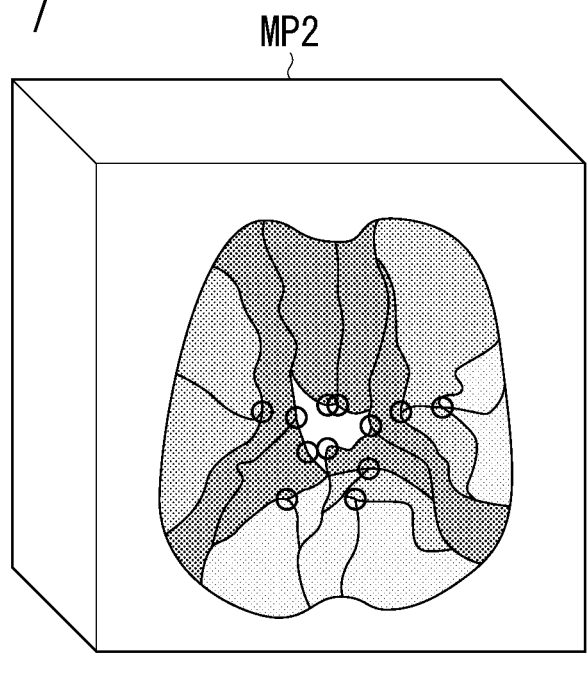
FIG. 7 is a diagram showing an example of a blood vessel-dominated region map.

FIG. 7 is a diagram showing an example of the blood vessel-dominated region map MP2. In the shown example, the blood vessel-dominated region map MP2 when all of the plurality of seed points S are set as expanded seed points S #is shown. Thus, the entire region of the brain can be color-coded using all seed points S and the user can be allowed to understand a region dominated by each blood vessel branching from the cerebral artery.

Figure 8:
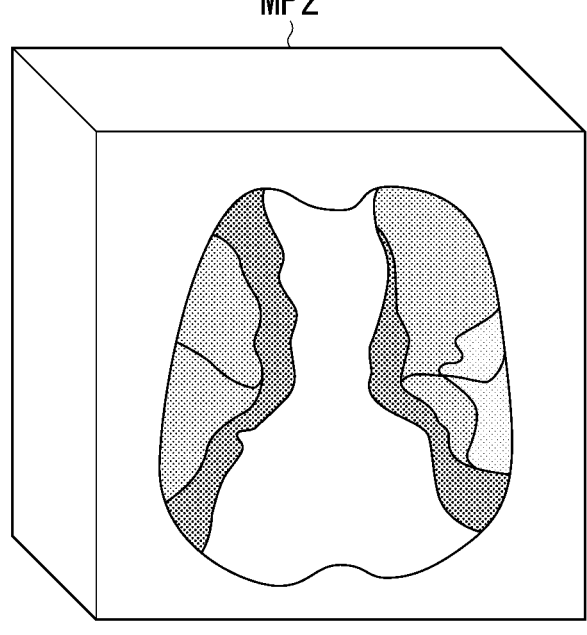
FIG. 8 is a diagram showing another example of a blood vessel-dominated region map.

FIG. 8 is a diagram showing another example of a blood vessel-dominated region map MP2. In the shown example, the blood vessel-dominated region map MP2 when some of the plurality of seed points S are set as expanded seed points S #is shown. Thus, only a specific region (for example, a region dominated by a middle cerebral artery) can be color-coded using only some seed points S.

According to the above-described first embodiment, the processing circuitry 120 acquires a multi-time-phase contrast CT image IMG1 (an example of a "medical image in which an artery is imaged") which is a CT image of the patient's brain into which the contrast medium has been injected. The processing circuitry 120 generates a cerebral artery mask image IMG2 on the basis of the multi-time-phase contrast CT image IMG1, and further detects the branch point B of the cerebral artery on the cerebral artery mask image IMG2. The processing circuitry 120 identifies a dominated region dominated by the branched blood vessel on the downstream side of the branch point B and generates a blood vessel-dominated region map MP2 by visualizing the dominated region of each branched blood vessel. Also, the processing circuitry 120 causes the display 113a to display the blood vessel-dominated region map MP2. Thus, by providing the user with not only the six cerebral arteries but also the dominated region of each blood vessel further branching therefrom as a blood vessel-dominated region map MP2, the user can be allowed to understand information about perfusion of more distal blood vessels and smaller brain regions. As a result, the user can, for example, identify clogged blood vessels that cause ischemia when a small infarct occurs at a deep position in the brain, identify blood vessels that nourish brain tumors and need to be embolized, or identify a blood vessel that is less affected by blood flow reduction or thrombus due to endovascular treatment and can be easily used for treatment, which can be used as various determination materials for diagnosis.

Second Embodiment

Hereinafter, the second embodiment will be described. The second embodiment is different from the first embodiment in that, for the purpose of generating a blood vessel-dominated region map MP2 with a smaller calculation amount than in the first embodiment, not all blood vessels branching from the six cerebral arteries become a processing target, but only some of the blood vessels branching from the six cerebral arteries designated by the user become a processing target. Hereinafter, differences from the first embodiment will be mainly described and content identical to that of the first embodiment will be omitted. Also, in the description of the second embodiment, parts identical to those of the first embodiment are denoted by the same reference signs.

FIG. 9 is a flowchart showing a flow of a series of processing steps of processing circuitry 120 according to the second embodiment. In the present flowchart, as an example, it is assumed that a medical image diagnostic device is an X-ray CT device and a medical image is a CT image.

First, the acquisition function 121 is performed to acquire a multi-time-phase contrast CT image IMG1 from the X-ray CT device via the communication interface 111 (step S200).

When the multi-time-phase contrast CT image IMG1 is acquired, the generation function 123 is performed to generate a contrast delay time map MP1 on the basis of the multi-time-phase contrast CT image IMG1 (step S204).

On the other hand, when the multi-time-phase contrast CT image IMG1 is acquired, the detection function 122 is performed to detect the branch point B of the artery of the brain on the basis of the multi-time-phase contrast CT image IMG1 and generate an arterial branch point list LT on the basis of the branch point B (step S206).

Subsequently, the setting function 124 is performed to set a part of the artery as a blood vessel of interest (step S208). For example, when the user has selected a desired blood vessel desired to visualize the blood vessel-dominated region from a list in which the blood vessel names are stored in a database via the input interface 112, the setting function 124 may be performed to set the blood vessel selected by the user as a blood vessel of interest. Also, when a setting file in which a blood vessel desired to be visualized is stored is stored in the memory 114 in advance, the setting function 124 may be performed to set a blood vessel of interest by reading a setting file stored in the memory 114.

Subsequently, the setting function 124 is performed to set the seed point S located on the blood vessel of interest and the seed point S located downstream of the blood vessel of interest among the plurality of seed points S whose coordinate points are stored in the arterial branch point list LT as expanded seed points S #, which are starting points of the region expansion method on the contrast delay time map MP1 (step S210).

For example, when a middle cerebral artery is set as the blood vessel of interest, the setting function 124 is performed to set the seed point S of the middle cerebral artery origin and the downstream seed point S #as the expanded seed points S #.

Subsequently, the identification function 125 is performed to identify the dominated region of each branched blood vessel on the basis of the expanded seed point S #set on the contrast delay time map MP1 and generate a blood vessel-dominated region map MP2 by visualizing the dominated region of each branched blood vessel (step S212). Because the seed point S located on the blood vessel of interest and the seed point S located downstream of the blood vessel of interest are set as the expanded seed point S #on the contrast delay time map MP1, a blood vessel-dominated region map MP2 is generated by the blood vessel of interest and its downstream-dominated region. Thus, the processing load (calculation amount and calculation time of the processing circuitry 120) related to the generation of the blood vessel-dominated region map MP2 can be reduced by setting the region of interest.

Subsequently, the output control function 126 causes the display 113a of the output interface 113 to display the blood vessel-dominated region map MP2 (step S214). Also, the output control function 126 may be performed to transmit the blood vessel-dominated region map MP2 to an external display device via the communication interface 111 in addition to or in place of displaying the blood vessel-dominated region map MP2 on the display 113a. With this, the process of the present flowchart ends.

According to the above-described second embodiment, the processing circuitry 120 sets some of the blood vessels branching from the six cerebral arteries as a blood vessel of interest, identifies the blood vessel of interest and its downstream-dominated region, and generates a blood vessel-dominated region map MP2 by visualizing dominated regions. By setting the blood vessel of interest in this way, the blood vessel-dominated region map MP2 can be generated with a smaller calculation amount than in the first embodiment.

Third Embodiment

Hereinafter, a third embodiment will be described. The third embodiment is different from the first or second embodiment in that, for the purpose of generating a blood vessel-dominated region map MP2 with a smaller calculation amount than in the first embodiment, not all blood vessel-dominated regions branching from the six cerebral arteries are identified, but only some dominated regions designated by the user are identified. Hereinafter, differences from the first embodiment and the second embodiment will be mainly described and the description of parts identical to those of the first embodiment and the second embodiment will be omitted. Also, in the description of the third embodiment, parts identical to those of the first or second embodiment are denoted by the same reference signs.

FIG. 10 is a flowchart showing a flow of a series of processing steps of processing circuitry 120 according to the third embodiment. In the present flowchart, as an example, it is assumed that a medical image diagnostic device is an X-ray CT device and a medical image is a CT image.

First, am acquisition function 121 acquires a multi-time-phase contrast CT image IMG1 from the X-ray CT device via the communication interface 111 (step S300).

When the multi-time-phase contrast CT image IMG1 is acquired, a generation function 123 is performed to generate a contrast delay time map MP1 on the basis of the multi-time-phase contrast CT image IMG1 (step S304).

On the other hand, when the multi-time-phase contrast CT image IMG1 is acquired, a detection function 122 is performed to detect the branch point B of the artery of the brain on the basis of the multi-time-phase contrast CT image IMG1 and generate an arterial branch point list LT on the basis of the branch point B (step S306).

Subsequently, a setting function 124 is performed to set a desired region to be visualized as a blood vessel-dominated region as a region of interest (step S308). For example, it is assumed that the user draws and sets a closed curved surface on the multi-time-phase contrast CT image IMG1 or on the contrast delay time map MP1 via an input interface 112. In this case, the setting function 124 may be performed to set the closed curved surface set by the user as the region of interest. A shape or size of the region of interest can be arbitrarily set by the user, but a size of the region of interest is preferably approximately half or less of the whole brain.

Also, when a setting file in which a brain region (for example, the frontal lobe, motor cortex, visual cortex, or the like) desired to be visualized is stored in a memory 114 in advance, the setting function 124 may be performed to read the setting file stored in the memory 114 and further set a region of interest by adjusting a position or size to the brain shape of the target patient.

Subsequently, the setting function 124 is performed to set a seed point S located on the region of interest and a seed point S located upstream of the region of interest from among the plurality of seed points S whose coordinate points are stored in the arterial branch point list LT as an expanded seed point S #, which is the starting point of the region expansion method on the contrast delay time map MP1 (step S310).

Figure 11:
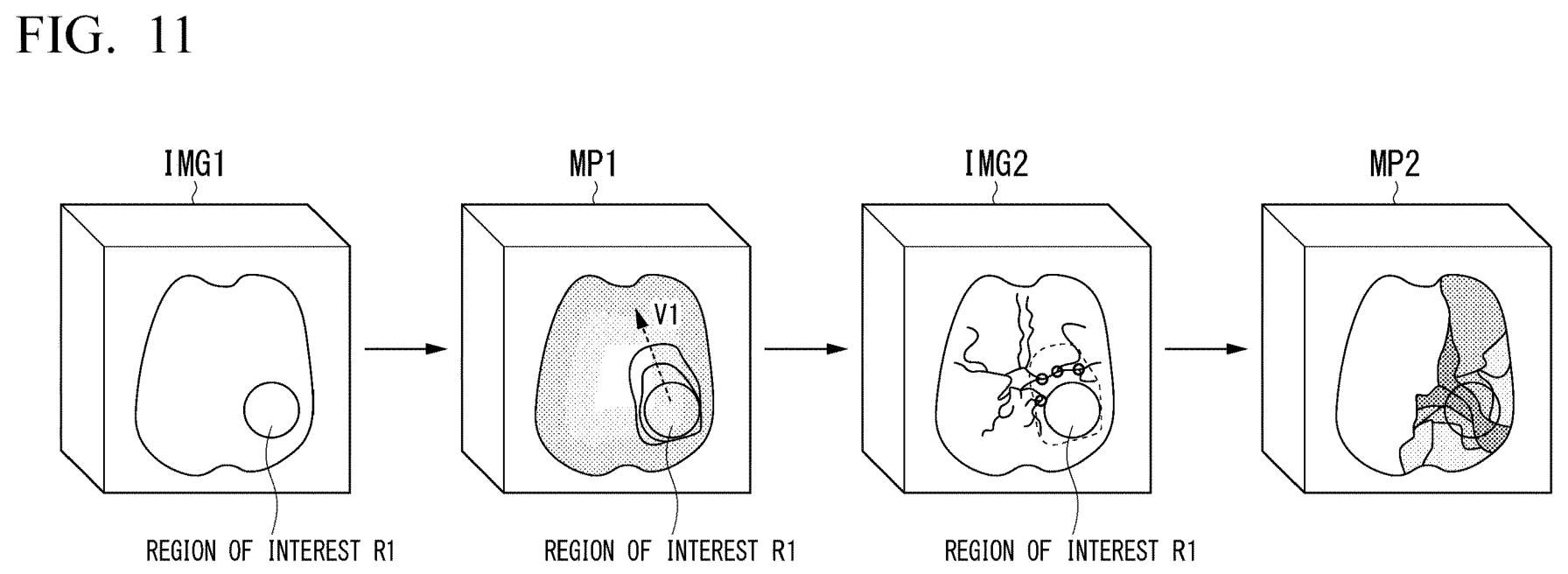

FIG. 11 is a diagram schematically showing a series of flows until a blood vessel-dominated region map MP2 is generated from the multi-time-phase contrast CT image IMG1. In FIG. 11, R1 denotes a region of interest. In principle, the seed point S of the region of interest R1 and the seed point S located upstream of the region of interest are connected by tracing the pixel values close to each other in the contrast delay time map MP1. Therefore, when the region of interest R1 is set, the setting function 124 is performed to perform a region expansion method (region expansion to a region where the pixel values are close to each other and small) in the opposite direction (V1 in FIG. 11) from the region of interest R in the contrast delay time map MP1 and set the seed point S included in the region as the upstream seed point S. For example, when a spherical region of the occipital lobe is set as the region of interest R1, the setting function 124 is performed to perform a region expansion method in the opposite direction from the region of interest R1 and set an upstream seed point S.

Subsequently, an identification function 125 is performed to identify a dominated region of each branched blood vessel on the basis of the expanded seed point S #set on the contrast delay time map MP1 and generate a blood vessel-dominated region map MP2 by visualizing the dominated region of each branched blood vessel (step S312).

Subsequently, an output control function 126 causes a display 113a of an output interface 113 to display the blood vessel-dominated region map MP2 (step S314). Also, the output control function 126 may be performed to transmit the blood vessel-dominated region map MP2 to an external display device via a communication interface 111 in addition to or in place of displaying the blood vessel-dominated region map MP2 on the display 113a. With this, the process of the present flowchart ends.

According to the above-described third embodiment, the processing circuitry 120 sets a part of the brain as a blood vessel of interest, identifies a region of interest and its upstream-dominated region, and generates a blood vessel-dominated region map MP2 by visualizing dominated regions. By setting the region of interest in this way, the blood vessel-dominated region map MP2 can be generated with a smaller calculation amount than in the first embodiment.

Fourth Embodiment

Hereinafter, a fourth embodiment will be described. The fourth embodiment is different from the above-described first to third embodiments in that a blood vessel-dominated region map MP2 is generated using only a branch point B without using a seed point S. Hereinafter, differences from the first to third embodiments will be mainly described and the description of parts identical to those of the first to third embodiments will be omitted. Also, in the description of the fourth embodiment, parts identical to those of any one of the first to third embodiments are denoted by the same reference signs.

Figure 12:
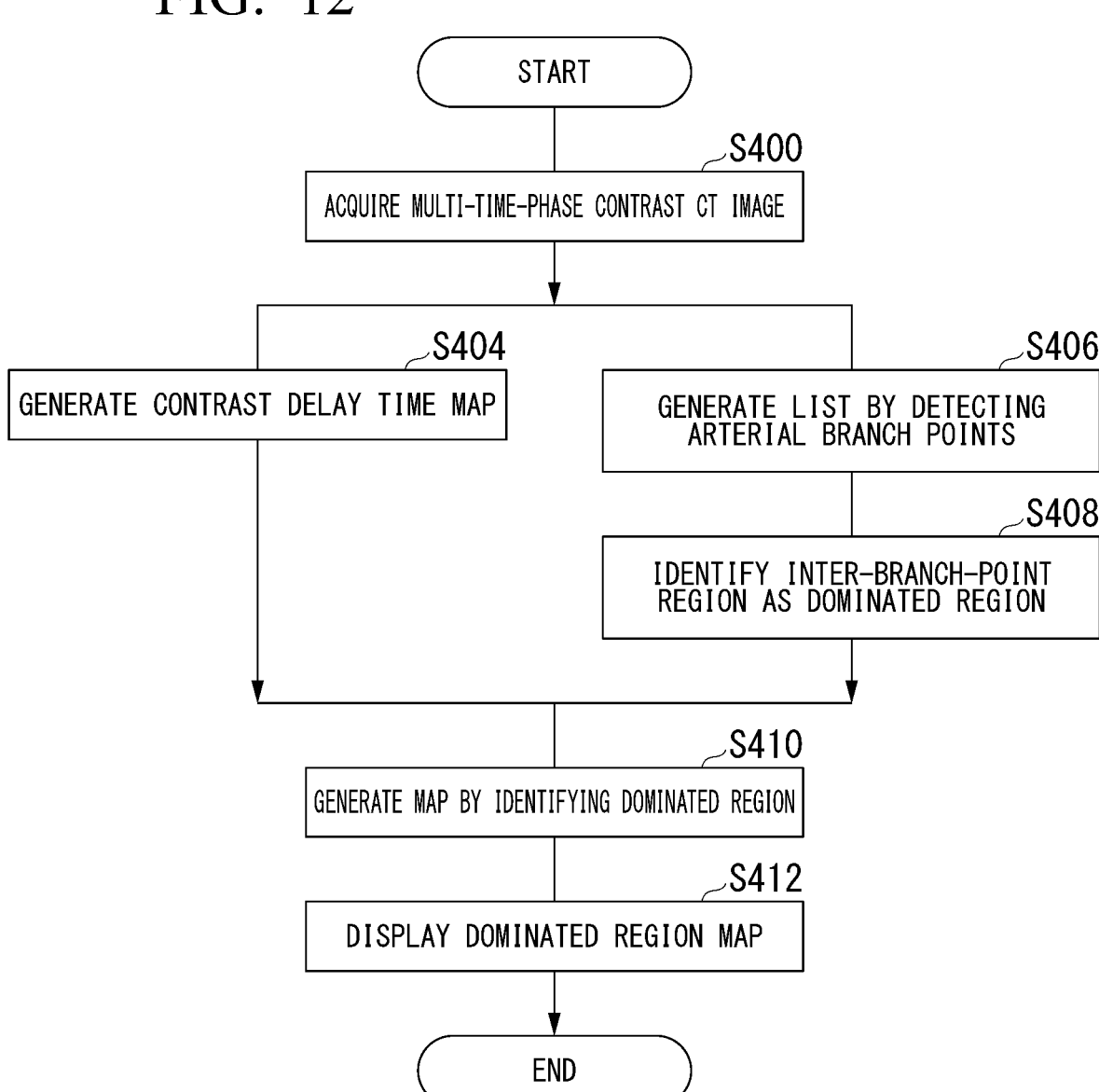
FIG. 12 is a flowchart showing a flow of a series of processing steps of processing circuitry according to a fourth embodiment.

FIG. 12 is a flowchart showing a flow of a series of processing steps of processing circuitry 120 according to the fourth embodiment. In the present flowchart, as an example, it is assumed that a medical image diagnostic device is an X-ray CT device and a medical image is a CT image.

First, an acquisition function 121 is performed to acquire a multi-time-phase contrast CT image IMG1 from the X-ray CT device via a communication interface 111 (step S400).

When the multi-time-phase contrast CT image IMG1 is acquired, a generation function 123 is performed to generate a contrast delay time map MP1 on the basis of the multi-time-phase contrast CT image IMG1 (step S404).

On the other hand, when the multi-time-phase contrast CT image IMG1 is acquired, a detection function 122 is performed to detect the branch point B of the artery of the brain on the basis of the multi-time-phase contrast CT image IMG1 and generates the arterial branch point list LT on the basis of the branch point B (step S406).

Figure 13:
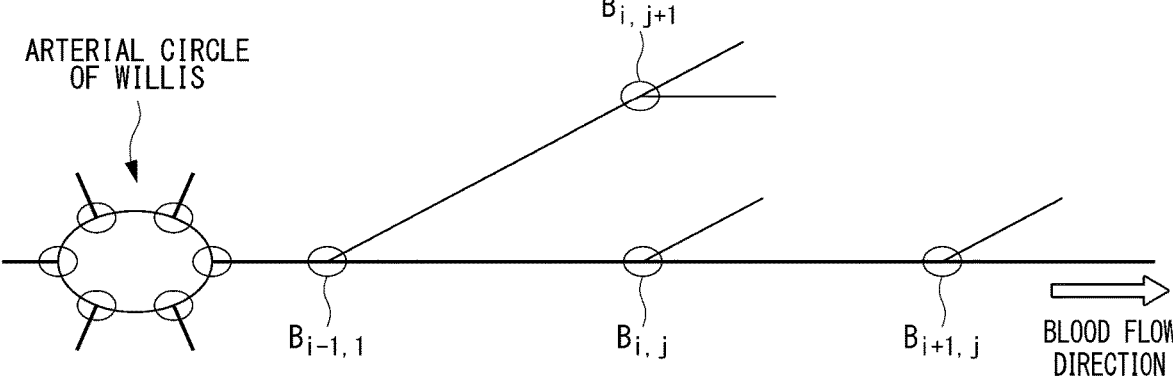
FIG. 13 is a diagram showing an example of an abstracted artery without a seed point.
Figure 14:
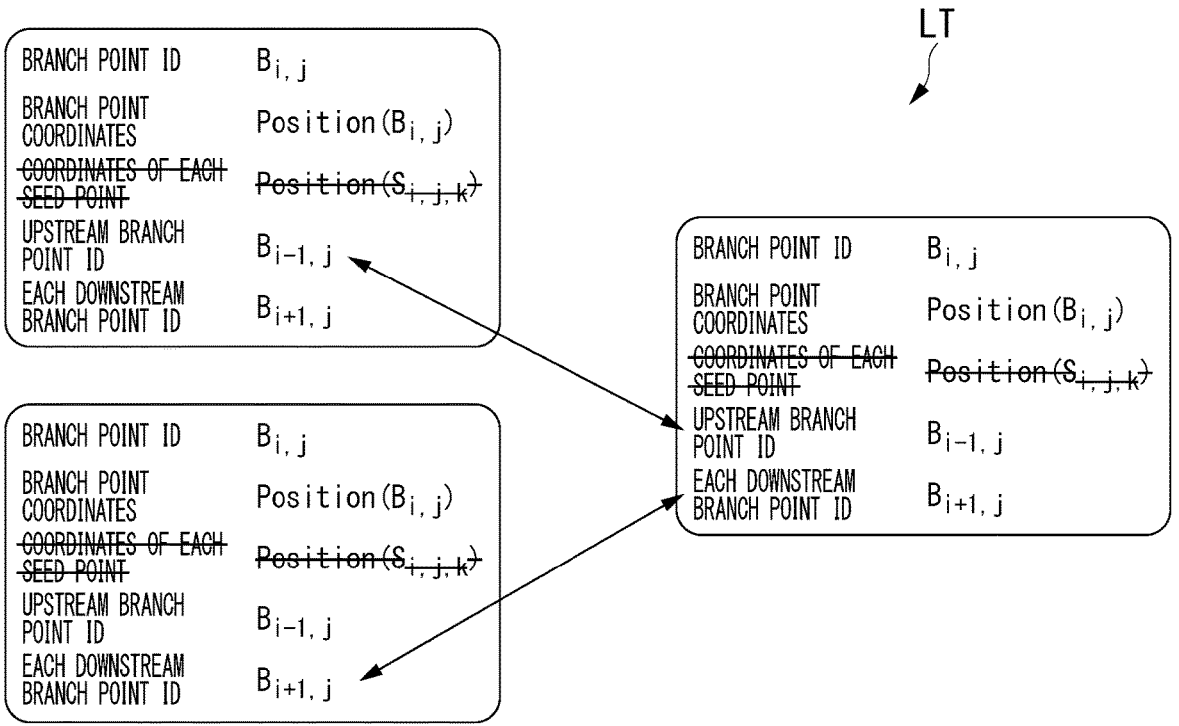
FIG. 14 is a diagram showing an example of an arterial branch point list without a seed point.

FIG. 13 is a diagram showing an example of an abstracted artery without a seed point S and FIG. 14 is a diagram showing an example of an arterial branch point list LT without a seed point S. As shown in FIG. 13, only branch point B is detected on the artery. Also, as shown in FIG. 14, the arterial branch point list LT has information about a branch point ID, branch point coordinates, an upstream branch point ID, and a downstream branch point ID for each branch point and has information about connections with upstream and downstream branch points. In the fourth embodiment, the seed point coordinates will be omitted.

Subsequently, an identification function 125 is performed to select two branch points B adjacent to each other from among the plurality of branch points B whose coordinate points are stored in the arterial branch point list LT and identify a region located between the two branch points B (hereinafter referred to as a branch point region) as a dominated region of the branch points B on the upstream side of the two branch points B (step S408). Exclusively, the distance between adjacent branch points B is short and the blood vessels do not significantly bend therebetween. Thus, a region between the branch points can be regarded as a dominated region dominated by upstream branch points.

Figure 15:
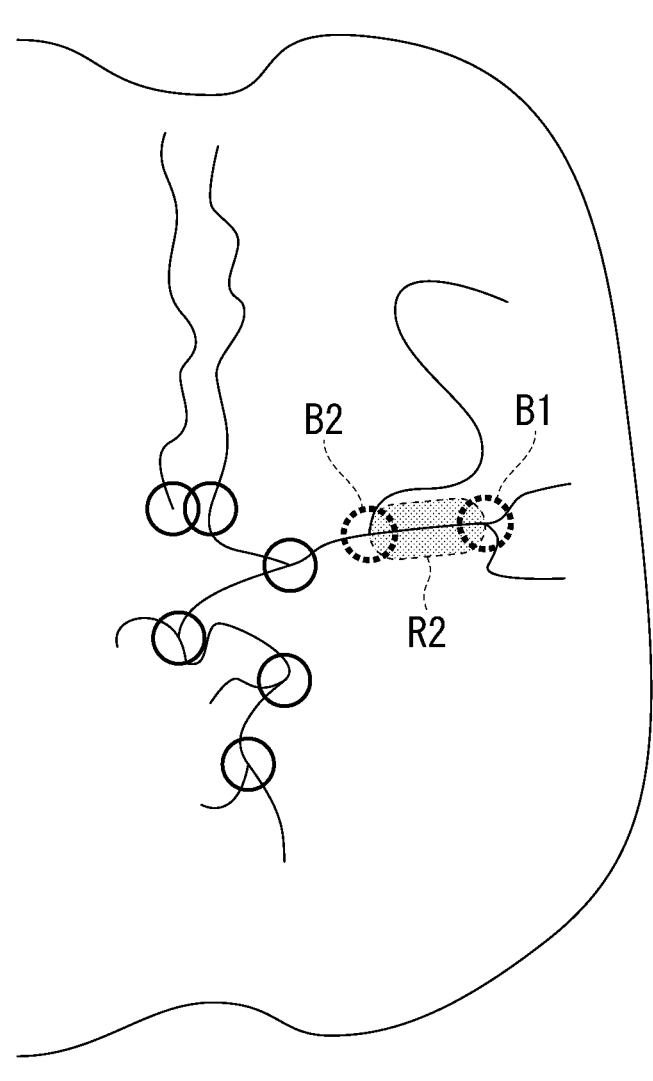
FIG. 15 is a diagram for describing a method of identifying a region between branch points.

FIG. 15 is a diagram for describing a method of identifying a region between branch points. For example, the identification function 125 may be performed to connect the coordinates of two branch points B1 and B2 adjacent to each other with a straight line and identify a set of pixels R2 overlapping the straight line as an inter-branch-point region. Also, the identification function 125 may be performed to identify a set of pixels overlapping a predefined shape having the coordinates of the two branch points B1 and B2 as parameters as the inter-branch-point region. For example, the inter-branch-point region may be defined so that the center points of the top surface and the bottom surface of the cylinder are determined by the coordinates of the two branch points B in a cylindrical shape having a diameter of 2 [mm]. By similarly setting the region between all branch points B as the inter-branch-point region, it is possible to identify the dominated region of all branched blood vessels and generate the blood vessel-dominated region map MP2 of all branched blood vessels. The branch point B1 is an example of a "first branch point" and the branch point B2 is an example of a "second branch point."

Subsequently, the identification function 125 is performed to execute a region expansion method with the contrast delay time map MP1 using the inter-branch-point region as the initial region and therefore generate the blood vessel-dominated region map MP2 by visualizing each inter-branch-point region as the dominated region (step S410).

Subsequently, an output control function 126 causes a display 113*a* of an output interface 113 to display the blood vessel-dominated region map MP2 (step S412). Also, the output control function 126 may be performed to transmit the blood vessel-dominated region map MP2 to an external display device via a communication interface 111 in addition to or in place of displaying the blood vessel-dominated region map MP2 on the display 113*a*. With this, the process of the present flowchart ends.

According to the above-described fourth embodiment, the processing circuitry 120 is performed to identify the inter-branch-point region, which is a region located between the two branch points B, as the dominated region of the branch points B located on the upstream side of the two branch points B and generate the blood vessel-dominated region map MP2 by visualizing dominated regions. Thus, by generating a blood vessel-dominated region map MP2 using only branch point B without using the seed point S and providing it to the user, the user can be allowed to understand information about perfusion of more distal blood vessels and smaller brain regions as in the first embodiment. As a result, the user can, for example, identify clogged blood vessels that cause ischemia when a small infarct occurs at a deep position in the brain, identify blood vessels that nourish brain tumors and need to be embolized, or identify a blood vessel that is less affected by blood flow reduction or thrombus due to endovascular treatment and can be easily used for treatment, which can be used as various determination materials for diagnosis.

OTHER EMBODIMENTS

Hereinafter, other embodiments will be described. Although the medical image processing device 100 acquires a multi-time-phase contrast CT image IMG1 from the X-ray CT device and generates a blood vessel-dominated region map of a branched blood vessel on the basis of the multi-time-phase contrast CT image IMG1 in the above-described embodiment, the present invention is not limited thereto. For example, the medical image processing device 100 may acquire a multi-time-phase contrast MR image from the MR device and generate a blood vessel-dominated region map of the branched blood vessel on the basis of the multi-time-phase contrast MR image.

A multi-time-phase contrast MR image is a set of MR images obtained when an MR device continuously images a portion of a patient into whom a contrast medium has been injected a plurality of times. In other words, the multi-time-phase contrast MR image is a set of MR images obtained when the MR device images a portion of a patient into whom the contrast medium has been injected at a plurality of times different from each other. That is, the medical image used for generating the blood vessel-dominated region map is not limited to the "CT image," but may be an "MR image."

Although the portion of the patient imaged by a medical image diagnostic device such as an X-ray CT device or an MR device (i.e., a portion that generates a blood vessel-dominated region map) is described as the "brain" in the above-described embodiment, the present invention is not limited thereto. For example, the portion of the patient imaged by the medical image diagnostic device may be other portions where arteries are distributed, such as the heart, lungs, liver, kidney, and small intestine.

While several embodiments of the present invention have been described above, these embodiments have been presented by way of example only, and are not intended to limit the scope of the inventions. These embodiments may be embodied in a variety of other forms. Various omissions, substitutions, and combinations may be made without departing from the spirit of the inventions. The inventions described in the accompanying claims and their equivalents are intended to cover such embodiments or modifications as would fall within the scope and spirit of the inventions.

The following appendixes are disclosed as aspects and selective features of the invention in relation to the above embodiment.

Appendix 1

A medical image processing device including:

an acquisition unit configured to acquire a medical image obtained by imaging at least an artery;

a detection unit configured to detect a branch point of the artery on the basis of the medical image;

an identification unit configured to identify a dominated region of the artery on a downstream side of the branch point in the medical image; and a display control unit configured to cause a display to display the dominated region.

Appendix 2

The medical image processing device may further include a setting unit configured to set a part of the artery on the medical image as a blood vessel of interest. The identification unit may identify the dominated region on the basis of the blood vessel of interest.

Appendix 3

The setting unit may set a seed point with respect to each blood vessel branching at the branch point. The identification unit may identify the dominated region on the basis of the seed point on the blood vessel of interest and the seed point located downstream of the blood vessel of interest.

Appendix 4

The medical image processing device may further include a setting unit configured to set a region of interest in the medical image. The identification unit may identify the dominated region on the basis of the region of interest.

Appendix 5

The setting unit may set a seed point with respect to each blood vessel branching at the branch point. The identification unit may identify the dominated region on the basis of the seed point in the region of interest and the seed point located upstream of the blood vessel of interest.

Appendix 6

The detection unit may detect a first branch point and a second branch point adjacent to each other. The identification unit may identify a region between the first branch point and the second branch point as the dominated region.

Appendix 7

The artery may be a cerebral artery. The identification unit may identify a dominated region of the artery located downstream of an artery circle of Willis and located on a downstream side of the branch point.

Appendix 8

The medical image processing device may further include a generation unit configured to generate a contrast delay time map in which a delay period of time of a contrast medium injected into the artery is set as a pixel value on the basis of the medical image. The identification unit may identify a dominated region of the artery on the contrast delay time map using a region expansion method.

Appendix 9

A medical image processing method to be executed using a computer, the medical image processing method including:

acquiring a medical image obtained by imaging at least an artery;

detecting a branch point of the artery on the basis of the medical image;

identifying a dominated region of the artery on a downstream side of the branch point in the medical image; and causing a display to display the dominated region.

Appendix 10

A computer-readable non-transitory storage medium storing a program for causing a computer to:

acquire a medical image obtained by imaging at least an artery;

detect a branch point of the artery on the basis of the medical image;

identify a dominated region of the artery on a downstream side of the branch point in the medical image; and cause a display to display the dominated region.

What is claimed is:

1. A medical image processing device comprising:

processing circuitry configured to acquire a medical image obtained by imaging at least an artery;

detect a branch point of the artery on the basis of the medical image;

identify a dominated region of the artery on a downstream side of the branch point in the medical image;

cause a display to display the dominated region;

derive a time density curve on the basis of a change over time in a luminance value of each pixel of the medical image;

generate a contrast delay time map in which a delay period of time of a contrast medium injected into the artery is set as a pixel value on the basis of the time density curve; and identify a dominated region of the artery on the contrast delay time map using a region expansion method.

2. The medical image processing device according to claim 1, wherein the processing circuitry is further configured to set a part of the artery on the medical image as a blood vessel of interest, and identify the dominated region on the basis of the blood vessel of interest.

3. The medical image processing device according to claim 2, wherein the processing circuitry is further configured to set a seed point with respect to each blood vessel branching at the branch point; and identify the dominated region on the basis of the seed point on the blood vessel and of interest the seed point located downstream of the blood vessel of interest.

4. The medical image processing device according to claim 1, wherein the processing circuitry is further configured to set a region of interest in the medical image; and identify the dominated region on the basis of the region of interest.

5. The medical image processing device according to claim 4, wherein the processing circuitry is further configured to set a seed point with respect to each blood vessel branching at the branch point; and identify the dominated region on the basis of the seed point in the region of interest and a seed point located upstream of a blood vessel of interest.

6. The medical image processing device according to claim 1, wherein the processing circuitry is further configured to detect a first branch point and a second branch point adjacent to each other; and identify a region between the first branch point and the second branch point as the dominated region.

7. The medical image processing device according to claim 1, wherein the artery is a cerebral artery, and wherein the processing circuitry further identifies a dominated region of the artery located downstream of an artery circle of Willis and located on a downstream side of the branch point.

8. A medical image processing method to be executed using a computer, the medical image processing method comprising:

acquiring a medical image obtained by imaging at least an artery;

detecting a branch point of the artery on the basis of the medical image;

identifying a dominated region of the artery on a downstream side of the branch point in the medical image;

causing a display to display the dominated region;

deriving a time density curve on the basis of a change over time in a luminance value of each pixel of the medical image;

generating a contrast delay time map in which a delay period of time of a contrast medium injected into the artery is set as a pixel value on the basis of the time density curve; and identifying a dominated region of the artery on the contrast delay time map using a region expansion method.

9. A computer-readable non-transitory storage medium storing a program for causing a computer to:

acquire a medical image obtained by imaging at least an artery;

detect a branch point of the artery on the basis of the medical image;

identify a dominated region of the artery on a downstream side of the branch point in the medical image;

cause a display to display the dominated region;

derive a time density curve on the basis of a change over time in a luminance value of each pixel of the medical image;

generate a contrast delay time map in which a delay period of time of a contrast medium injected into the artery is set as a pixel value on the basis of the time density curve; and identify a dominated region of the artery on the contrast delay time map using a region expansion method.

10. The medical image processing device according to claim 1, wherein the processing circuitry is further configured to set a seed point with respect to each blood vessel branching at the branch point;

generate a blood vessel-dominated region map by color-coding each region of the contrast delay time map with a different pixel value for each the seed point on the contrast delay time map using the region expansion method; and cause the display to display the blood vessel-dominated region map.

\* \* \* \* \*